US012539153B2

(12) United States Patent
Mei-Dan et al.

(10) Patent No.: US 12,539,153 B2
(45) Date of Patent: Feb. 3, 2026

(54) ORTHOPEDIC PLATE SYSTEM

(71) Applicant: MDS II LLC, Boulder, CO (US)

(72) Inventors: Omer Mei-Dan, Boulder, CO (US); Jason W. Stoneback, Fort Lupton, CO (US); Jacob Segil, Boulder, CO (US); Benjamin Carnicelli, Denver, CO (US)

(73) Assignee: HEAPSI, LLC, Boulder, CO (US)

( * ) Notice: Subject to any disclaimer, the term of this patent is extended or adjusted under 35 U.S.C. 154(b) by 275 days.

(21) Appl. No.: 18/137,879

(22) Filed: Apr. 21, 2023

(65) Prior Publication Data

US 2023/0338072 A1 Oct. 26, 2023

Related U.S. Application Data

(60) Provisional application No. 63/333,866, filed on Apr. 22, 2022.

(51) Int. Cl.
*A61B 17/80* (2006.01)

(52) U.S. Cl.
CPC ...... *A61B 17/8085* (2013.01); *A61B 17/8033* (2013.01); *A61B 17/8057* (2013.01)

(58) Field of Classification Search
CPC .. A61B 17/80; A61B 17/8057; A61B 17/8085
See application file for complete search history.

(56) References Cited

U.S. PATENT DOCUMENTS

| | | | | |
|---|---|---|---|---|
| 2015/0289910 A1 | 10/2015 | Mirghasemi et al. | | |
| 2018/0036050 A1* | 2/2018 | Mishra | .................. | A61B 17/80 |
| 2018/0206893 A1* | 7/2018 | Biedermann | .......... | A61B 17/80 |

OTHER PUBLICATIONS

International Search Report and Written Opinion issued Sep. 1, 2023 in corresponding application PCT/US2023/019449, filed Apr. 21, 2023.
Cronier, P. et al., "The concept of locking plates" (2010) Orthopaedics & Traumatology: Surgery & Research 96S: pp. S17-S36.
Acumed LLC "Pelvic Plating System—Surgical Technique" (2018) 64 pages.

* cited by examiner

*Primary Examiner* — Si Ming Ku
(74) *Attorney, Agent, or Firm* — Brownstein Hyatt Farber Schreck, LLP

(57) ABSTRACT

Embodiments are directed to an orthopedic fixation system that includes first and second plates each defining a clamp positioned at an end of the plate and comprising a first hole, a body portion extending from the clamp and comprising one or more holes, and one or more raised features positioned along the body portion. The clamp of the first plate is configured to couple with the body portion of the second plate. The first hole is configured to align with a second hole of the one or more holes. The first and second plates are rigidly coupled when an orthopedic screw engages with the first hole and the second hole and are coupled to a user.

15 Claims, 8 Drawing Sheets

ORTHOPEDIC PLATE SYSTEM

CROSS-REFERENCE TO RELATED APPLICATION

This application is a nonprovisional patent application of and claims the benefit under 35 U.S.C. § 119(e) of U.S. Provisional Patent Application No. 63/333,866, filed Apr. 22, 2022, and titled “Orthopedic Plate System”, the contents of which are incorporated herein by reference in its entirety.

FIELD

The described embodiments relate generally to a medical device for treating orthopedic fractures and more particularly, the present embodiments relate to orthopedic plates for treating bone fractures.

BACKGROUND

Orthopedic plates can be used to internally fix bone fractures. An orthopedic plate can be screwed or otherwise fixed to portions of a fractured bone to stabilize the different portions relative to one another while the bone heals. Conventional orthopedic plates are available in a variety of shapes and sizes and may have shapes that mimic the shape of a particular bone so that a plate may conform to a bone or portion of a bone. For example, an orthopedic plate may have a curve that generally matches the curve of a bone to which the plate is affixed. In some cases, orthopedic plates may also be bendable and a surgeon may manipulate the plate during an operation to match the shape of the plate to the shape of a bone. However, even with a variety of differently shaped orthopedic plates, conventional plates may not have a desirable shape for treating some types of fractures. For example, the shape and/or anchoring hole locations on conventional plates may not align well with some fracture locations such as comminuted fractures.

SUMMARY

Embodiments are directed to an orthopedic fixation system that includes first and second plates. Each plate can define a clamp positioned at an end of the plate and comprising a first hole, a body portion extending from the clamp and comprising one or more holes, and one or more raised features positioned along the body portion. The clamp of the first plate can be configured to couple with the body portion of the second plate. The first hole can be configured to align with a second hole of the one or more holes. In some cases, the first and second plates are rigidly coupled when an orthopedic screw engages with the first hole and the second hole and is coupled to a user.

Embodiments are directed to an orthopedic plate system that includes a first plate defining a body portion, one or more holes positioned along the body portion, and one or more raised features positioned along the body portion. The orthopedic plate system can include a second plate defining a body portion, one or more raised features positioned along the body portion, and a clamp positioned at an end of the body portion and comprising a first hole. The clamp can be configured to couple to the body portion of the first plate. In some cases, the first hole is aligned with a second hole of the one or more holes when the clamp is coupled to the body portion of the first plate. In some cases, the first and second holes are configured to accept an orthopedic screw.

Embodiments include an orthopedic plate that includes a body section having a length that is greater than a width. The body section can define a first side extending along the length of the body section and a second side opposite the first side and extending along the length of the body section. The body section can also define a first set of locking features positioned along the first side, where the first set of locking features comprises first semi-circular holes extending through a thickness of the body section. The body section can define a second set of locking features positioned along the second side, where the second set of locking features comprises second semi-circular holes extending through a thickness of the body section. The holes of the first semi-circular holes may alternate with holes of the second semi-circular holes.

BRIEF DESCRIPTION OF THE DRAWINGS

The disclosure will be readily understood by the following detailed description in conjunction with the accompanying drawings, wherein like reference numerals designate like structural elements, and in which.

Figure 1:
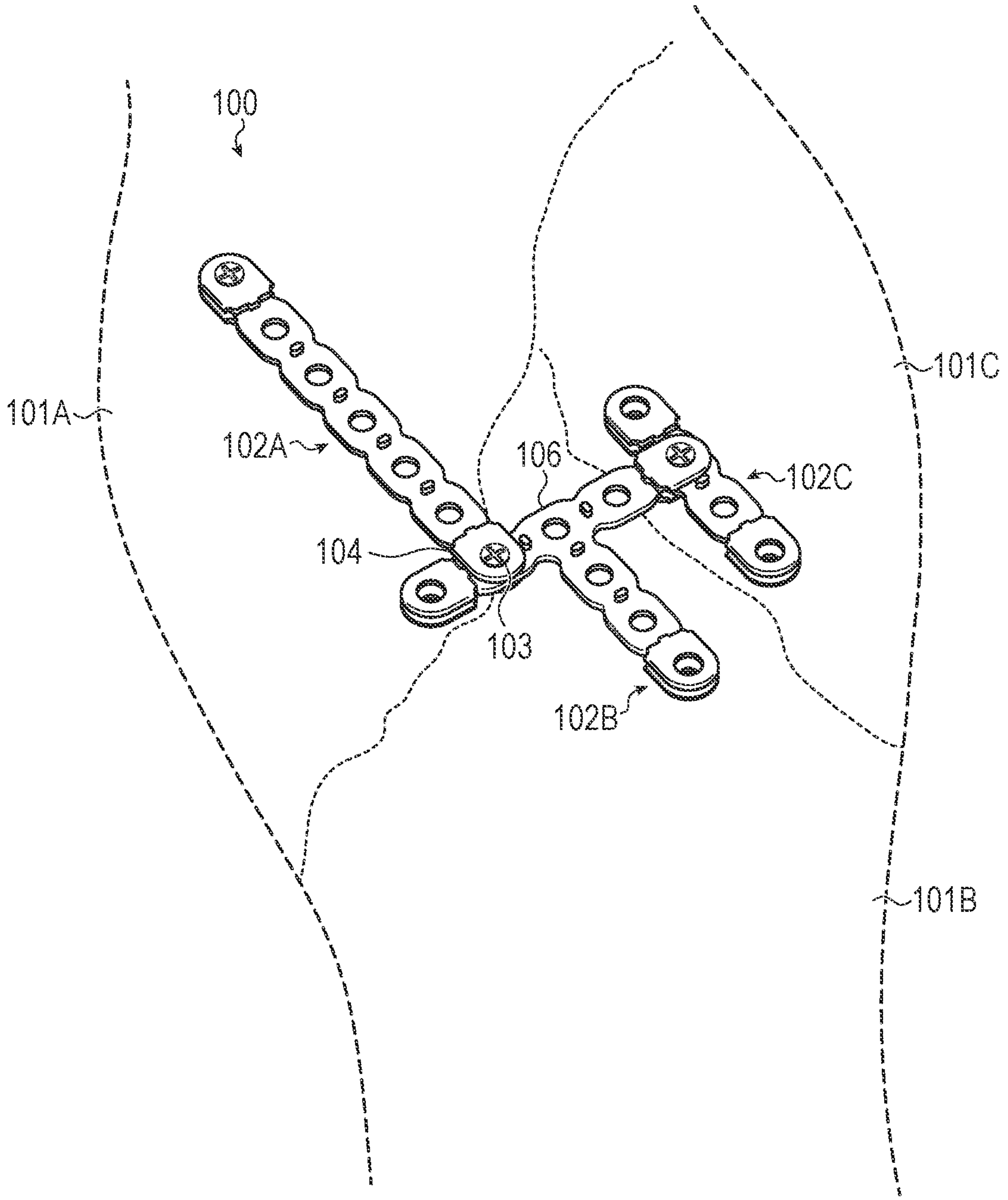
FIG. 1 shows an example of an orthopedic plate system being used to stabilize a comminuted fracture.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to an orthopedic plate system having various plates that can be assembled in a variety of orientations in order to create an assembled structure. The assembled structure can be tailored to a patient’s anatomy and/or fracture locations. Each plate includes coupling features that allow it to be coupled with another plate in a fixed relationship. In some cases, the plates can be coupled together and an orientation of the plates relative to one another can be adjusted, for example, based on a shape and/or fracture location(s) on a bone. Once a desired orientation of the plates has been set, a fastening mechanism, such as an orthopedic screw, can affix the plates to each other and/or affix the assembled plate structure to a bone. Thus, a single fastening mechanism may affix plates together and simultaneously anchor the plate structure to the bone. The plates can come in a variety of shapes and sizes and may include universal coupling features, which allow each plate to be connected to other plates. Accordingly, a surgeon (and/or other user) can select and assemble different plates to create an assembled structure customized to a particular bone shape or type and/or location of fractures within a bone.

In some cases, such as when a bone has a comminuted fracture, a surgeon may not have a single plate that conforms correctly to the patient's bone shape and/or has anchoring points in undesirable locations (such as an anchoring point located at or near a fracture). For example, when a bone is fractured in multiple locations, a conventional plate may have anchoring features (holes or other anchoring points) that do not align well with the fracture locations. In some cases, the conventional plate may have anchoring features that are positioned over the fracture locations; inserting an orthopedic screw into these locations may widen the fracture and prevent or delay healing. Accordingly, using conventional plates, a surgeon may need multiple independent anchored plates to fix a fracture. However, these independently anchored plates typically impart less structural integrity than using a single, properly anchored plate, leaving the fractured bone more susceptible to an injury. Similarly, using multiple disconnected plates results in longer implantation times and takes longer to heal.

The system and devices described herein include an interconnected assembly that can be formed from multiple different plates. Various plates can be coupled together, positioned in a desired orientation relative to each other and the bone, and then fixed with respect to each other and the bone to create a stabilized, interconnected assembly. Such a system may provide a surgeon with more options when treating fractures. For example, a surgeon may be able to select different lengths and/or shapes of plates and construct a plate assembly that has a desirable orientation with respect to both a shape of the fractured bone and/or the locations of the fracture(s).

In some cases, the plates can each include a clamp and a body portion. The clamp can couple to the body portion of another plate. In some examples, the clamp of a first plate slides over the body portion of a second plate. Sliding the clamp of the first plate over the body portion of the second plate restricts motion between the two plates in some directions while still allowing for relative motion between the plates in other directions. For example, sliding the clamp of the first plate over the body portion of the second plate allows the first and second plates to be rotated with respect to each other. Accordingly, a surgeon (or other user) may initially couple two plates together and rotate or otherwise adjust a relative orientation of the plates with respect to each other, for example, to align the assembly to a bone and/or fracture locations.

The plates can include one or more features that are configured to engage with an orthopedic screw, which can fix the plates with respect to each other to form a rigid assembly and/or fix the plates to the bone. In some cases the clamp and the body portion of each plate can include one or more holes that are configured to engage with an orthopedic screw. When the clamp of a first plate is engaged with (e.g., slid over) a body portion of a second plate, a hole in the clamp can align with a hole in the body portion. An orthopedic screw passes through the aligned holes, which can fix the plates with respect to each other and fix the assembly to the bone. In some cases, additional orthopedic screws can be engaged with other holes on the first and/or second plates to provide additional anchors to the bone. Accordingly, the rigid plate assembly may span multiple bone segments and align and fix these bone segments to heal.

Embodiments described herein are also directed to an orthopedic plate that includes locking features that are positioned along a side of the device. Conventional orthopedic plates include holes for engaging with an orthopedic screw and these holes are typically positioned within a body segment of the plate. Accordingly, a width of a conventional plate is larger than the holes that engage with the orthopedic screw. Further, conventional plates typically orient the holes along a centerline of the plate, which results in a spacing between the holes being larger than a diameter of the holes. In some cases, it may be desirable to have plates that are thinner than a diameter of the orthopedic screw and/or be able to position orthopedic screws closer together. For example, more closely positioned screws may be used to stabilize specific portions of a fractured bone that require a greater number of anchoring points.

In some cases, an orthopedic plate can include locking features that are positioned along one or more sides of the plate. The locking features can be semi-circular holes that are formed along one or more edges. As used herein, the term "semi-circular hole" is used to refer to an opening that interrupts the edge of a plate. For example, a semi-circular whole may be an opening in the edge of a plate the defines a partial circular section (or other suitable shape) within the body of the plate and having an incomplete circular section. For example, the incomplete circular portion may be a circular portion that would extend past the edge of the plate. The semi-circular holes may allow the plate to be narrower since the plate does not completely surround an orthopedic anchor such as an orthopedic screw. Additionally or alternatively, the semi-circular holes can be configured in an alternating pattern on each side of the plate, which can allow the holes to be positioned closer together. With closer holes, the anchor density can be increased which may help to stabilize various portions of a fractured bone.

These and other embodiments are discussed below with reference to FIGS. 1-8. However, those skilled in the art will readily appreciate that the detailed description given herein with respect to these Figures is for explanatory purposes only and should not be construed as limiting.

FIG. 1 shows an example of an orthopedic plate assembly 100 being used to stabilize a comminuted fracture of a bone 101. The example comminuted fracture includes multiple bone segments 101. For example, the comminuted fracture may result in a first bone segment 101*a*, a second bone segment 101*b*, and a third bone segment 101*c*. The orthopedic plate system 100 can include multiple plates 102 that are coupled together to form the plate assembly 100. In the example, shown, the plate assembly 100 includes a first plate 102*a*, a second plate 102*b* and a third plate 102*c*. However, other numbers and/or combinations of plates can be used.

The plates 102 can be oriented to the bone 101 in a variety of ways. Some plates may be oriented over a single bone segment 101, while other plates may be oriented over multiple bone segments. For example, the first plate 102*a* can be oriented and fixed to the first bone segment 101*a*, the second plate 102*b* may be oriented over the first, second, and third bone segments 101*a*, 101*b*, 101*c*, and the third plate 102*c* may be oriented over the third bone segment 101*c*. The second plate 102*b* can be coupled to each of the first, second, and third bone segments 101*a*, 101*b*, 101*c*, for example using multiple orthopedic screws 103. In other cases, different plates 102 of the orthopedic assembly 100 may each be positioned over multiple bone segments 101.

In some cases, the plates 102 may be assembled and oriented with respect to each other prior to fixing the plates with respect to each other and/or the bone 101. The plates may each include coupling mechanisms that can be used to attach the plates to each other prior to fixing the assembly and/or anchoring the assembly to the bone 101. The coupling mechanism can allow the relative position of the plates to the changed while the plates are positioned over the bone 101. For example, when initially coupled (prior to fixing the assembly or anchoring the plates to the bone), the first plate 102*a* may be moved within a range defined by the coupling mechanism. In some cases, this can include rotating the first plate 102*a* with respect to the second plate 102*b*, which can allow each of the plates 102 to be positioned with respect to each other and a corresponding bone segment 101. The coupling mechanism can be configured to allow different movements between the plates prior to fixing the assembly 100 and/or anchoring the assembly to the bone 101.

In some cases, a screw 103 can be used to fix the plates 102 without anchoring the plates to the bone 101. For example, the screw 103 may be a temporary screw that couples the first plate 102*a* to the second plate 102*b*, but does not engage with the bone. The temporary screw can be remove and replaced with a screw 103 that engages with the bone 101 to couple the assembly 100 to the bone 101.

In other cases, the screw 103 may be a permanent screw that couples multiple plates together without engaging the bone. Accordingly, in these examples, one or more screws 103 can be used to fix plates together while other screws 103 can be used to couple the plate assembly 100 to the bone 101. In some cases, the screw 103 can have multiple engagement states. For example, in a first state the screw can be engaged part way to couple multiple plates 102 together while not engaging with the bone. The screw can have a second state where it engages with the bone 101 to couple the plate assembly 100 to the bone 101. This may allow a user to construct and position a plate assembly 100 over a fractured bone prior to coupling the assembly 100 to the bone 101.

The orthopedic plates 102 can be fixed with respect to each other to create a rigid assembly 100 and/or may be each anchored to the bone 101. In some cases, orthopedic fasteners can be used to fix the plates 102 with respect to each other to create a rigid assembly 100 and anchor the plates to the bone 101. For example, the coupling mechanism can include a clamp 104 (only labeled on the first plate 102*a* for clarity) positioned on the end of the first plate 102*a* that couples to a body segment 106 (only labeled on the second plate 102*b* for clarity) of the second plate 102*b*. Each of the clamp 104 and the body segment 106 can include holes that align and are configured to accept an orthopedic screw. Engaging an orthopedic screw with the clamp 104 and the body segment 106 can fix the first plate 102*a* with respect to the second plate 102*b* and anchor the assembly 100 to the bone 101. Inserting an additional orthopedic screw through the coupling mechanism of the second plate 102*b* and the third plate 102*c* can fix the second and third plates 102*b*, 102*c* with respect to each other and further anchor the assembly 100 to the bone.

The orthopedic plates 102 can be fixed with respect to each other to create a rigid assembly in a variety of ways. In some cases, the orthopedic plates 102 can include threaded openings and threads on the orthopedic screw can engage with these openings to lock the plates 102 together. For example, the threads can be configured to compress a clamp on a first orthopedic plate 102 against a body section of a second orthopedic plate. In other examples, the orthopedic plates can have a set of mating grooves that fix the plates 102 in a relative orientation when they are engaged with each other.

In other cases, the orthopedic plates 102 can include openings that accept a fastener to fix the plates 102 in a specific orientation relative to each other. For example, each plate 102 can have semi-circular, oval, square, star, or other shaped holes that defines a positional relationship between a different plates 102. These embodiments can include a pin that is inserted through the opening and locked to the plates (e.g., using a cross-pin, nut, or other suitable mechanism). Accordingly, the plates 102 can be positioned in relative orientations in accordance with the shape of the opening and inserting a pin through the opening locks the plates in a fixed orientation. In some cases, the pin and/or locking mechanism can also be used to set a distance between the plates. For example, the plates can be touching or offset by a distance.

In other examples, a first plate may have a first set of mating features such as a set of protrusions and a second plate may have a second set of mating features such as a set of apertures. The protrusions of the first plate can be configured to engage with the apertures of the second plate. For example, the protrusions extend through the apertures. The orientation of the plate can be adjusted by changing which protrusions engage with which apertures. Additionally, an orthopedic screw or other fastening mechanism (e.g., nut, toggle, pin, etc.) can be used to secure the plates together after the protrusions of a first plate are engaged with apertures of a second plate. In these cases, the potential orientations of the plates with respect to each other can be defined by the number and/or configurations of the apertures and/or protrusions on the plates.

As used herein, an orthopedic screw engaging with one or more plates is meant to cover a variety of engagement mechanisms. In some cases, one or more of the orthopedic plates 102 can include threaded holes and threads on an orthopedic screw 103 (e.g., threads on the head of an orthopedic screw) engage with the threaded holes. The threaded engagement of an orthopedic screw 103 may fix one or more of the plates 102 with respect to the bone and/or with respect to each other. In other cases, one or more of the orthopedic plates 102 can include unthreaded holes and a threaded body portion of the orthopedic screw 103 may pass through these holes while a head of the orthopedic screw 103 engages with the plate 102. In these cases, the primary fixing mechanism may come from compression of the plate against another plate and/or the bone by the orthopedic screw. In some cases, various plates 102 can have different types of engagement mechanisms, for example a combination of threaded and unthreaded holes.

In some cases, coupling mechanisms can be configured to engage with locking orthopedic screws. As used herein the term "locking orthopedic screw" is used to define orthopedic screw that comprise features that lock a portion of the screw (e.g., the screw head) with respect to the plate as the screw is engaged with the plate. For example, the head of a locking screw can be configured to fix the plates 102 with respect to each other and lock the assembly 100 with respect to the bone. In other cases, an orthopedic screw may cause the clamp 104 to compress on the body segment 106, thereby locking the first plate 102*a* with respect to the second plate 102*b*. In other cases, the various plates 102 can be locked to each other in a variety of ways, as described herein.

The orthopedic plates 102 can be used with open surgical procedures, in which an incision is large enough for a surgeon to view the placement of the orthopedic plate(s) 102 and directly manipulate the orthopedic plate(s) 102. The orthopedic plates 102 described herein may also be used in percutaneous procedures where an incision may be kept smaller and the surgeon manipulates an orthopedic plate(s) 102 through the incision using one or more tools, but may not be able to directly view the orthopedic plate(s) 102. For example, an insertion tool may attach to a plate and be used to manipulate the plate through an incision during a percutaneous procedure. In some cases, the orientation of the insertion tool to the plate may be used to indicate a positioning of the orthopedic plate 102. For example the insertion tool may include a handle portion that remains outside of the patient while the orthopedic plate 102 is being positioned through an incision. The handle may align with the orthopedic plate 102 in a specific orientation so that the surgeon can determine the orientation of the orthopedic plate 102 based on the orientation of the handle. Additionally or alternatively, the orthopedic plates may be viewed using traditional radiographic procedures and/or include specific radiographic features to help position the orthopedic plate during a procedure.

The orthopedic plates 102 can be configured in a variety of sizes and shapes and different sized and shaped plates may be assembled together. A surgeon may choose different sized and shaped plates based on the shape of the bone, location of the fracture(s), number of anchoring points in each bone, among other factors. For example, the first plate 102*a* has a first configuration (e.g., straight shape with a first length), the second plate 102*b* has a second configuration (e.g., t-shape) and the third plate 102*c* has a third configuration (e.g., straight shape with second length). Accordingly, the assembly 100 can be constructed during an operation by a surgeon selecting the desired plates and coupling them together based on a variety of factors including the bone shape and/or location of the fracture(s).

The orthopedic plates 102 can include and/or be formed from medical grade materials. For example, the orthopedic plates 102 can be formed from medical grade allows such as stainless steel, titanium or any other suitable metal materials. Additionally or alternatively, the orthopedic plates can be formed or include other materials such as medical grade polymers, ceramics and so on. In some cases, one or more orthopedic plates 102 can include a combination of medical grade materials such as a combination of metal and polymer materials. In yet other cases, a first orthopedic plate 102 can be formed from a first material (or combination of materials) and a second orthopedic plate 102 can be formed from a second material (or combination of materials) that is different from the first.

Figure 2:
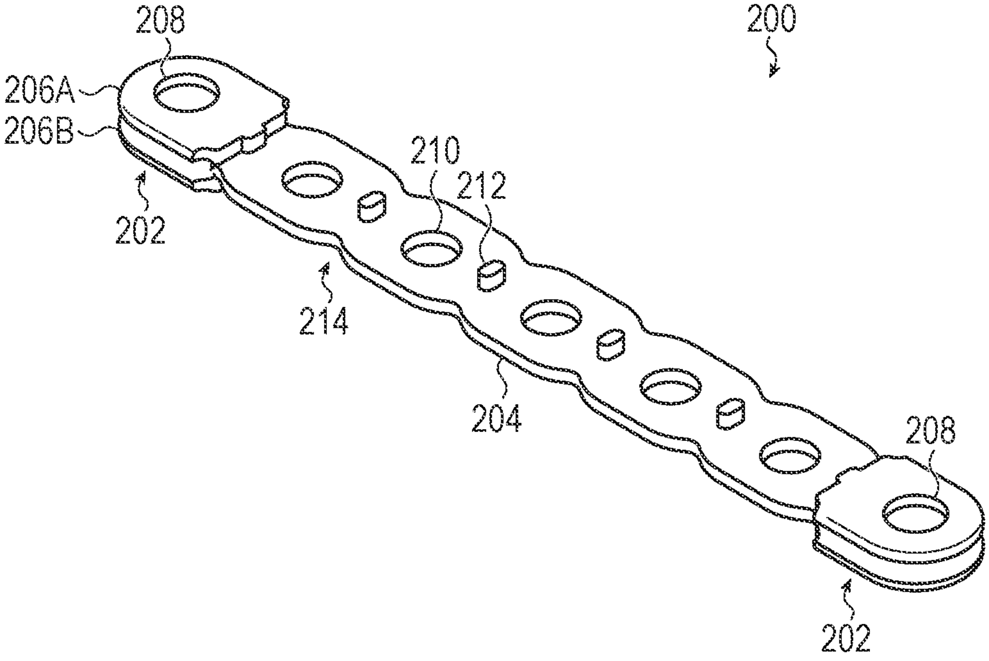
FIG. 2 shows an example of an orthopedic plate.

FIG. 2 shows an example orthopedic plate 200 that can be used to create an assembled plate system such as the orthopedic plate assembly 100. The orthopedic plate 200 is shown and described as a straight plate configuration, however the concepts described with respect to the plate 200 can be applied to different plate configurations such as plates with different lengths, shapes, sizes, or other variations.

The orthopedic plate 200 can include one or more clamps 202 and a body section 204 extending between the clamps 202. In some cases the clamps 202 can be configured to couple with a body section of a different plate. For example, as shown in FIG. 2, the clamps 202 can each include a first arm 206*a* that is offset from a second arm 206*b* (one of which is labeled for clarity). The arms 206 can be positioned over opposite sides of the body 204, when the plate 200 is coupled to another plate. In some cases, the configuration of the clamp 202 may define/constrain movement of the plate 200 with respect to another plate. For example, prior to fixing the plate 200 with respect to another plate, the clamp 202 can allow the plate 200 to be rotated with respect to the other plate, which may be used to configure an angular orientation of the plates. In other cases, one or more of the clamps 202 can have different configurations. For example, the clamp may have a single arm 206 that overlaps with the body section 204.

One or more of the clamps 202 can include a hole 208, which can be configured to engage with an orthopedic screw. In some cases, the clamp 202 can include a threaded hole 208 which engages with threads on an orthopedic screw such as a locking orthopedic screw. In these examples, the locking orthopedic screw may lock the plate 200 with respect to the bone, for example, in an offset relationship to the bone. In other cases, the clamp 202 can include other features for engaging with a locking orthopedic screw, such as a molded material around the hole 208 that is engaged by threads on an orthopedic screw. For example, the threads on the head may cut into the molded material to lock the orthopedic screw with respect to the plate. In yet other cases, the arms 206 can each define a threaded hole 208, such that an orthopedic screw engages with each arm of the clamp 202. Additionally or alternatively, the arms 206 can be configured to compress around a body portion of another plate, which may be used to fix the plate 200 to another plate. In some cases, threading on an orthopedic screw can be configured to cause the arms 206 to compress towards each other thereby clamping down on a body section of a second orthopedic plate.

In some cases, the plate 200 can include different types of clamps for example, a first end of the plate 200 can include a clamp 202 with two arms 206 and a second end of the plate 200 can include a clamp with a single arm 206. This may allow a single plate 200 to have different connection types. In some cases, one of more ends of a plate 200 can be configured to treat a wing fracture of the pelvic bone, and may include an end that extends over and/or wraps around a portion of the pelvic bone to secure the orthopedic plate 200 to the pelvic bone.

The body section 204 can include one or more holes 210 (one of which is labeled for clarity) which can align with the holes 208. When the holes 208 on the clamp 202 align with holes on a body section of another plate, the clamp 202 and body section can define a single hole that can be engaged by an orthopedic screw. In some cases, the holes 210 in the body sections can be unthreaded and the plate 200 is fixed to another plate by a clamping motion of the clamps 202 on the body. In other cases, the holes 210 can include features that fix the body section 204 with respect to a clamp of another plate. The body section 204 can include a material around the holes 210 that is engaged by an orthopedic screw. For example, the body section 204 can include a polymer material molded around the holes 210, clamps on a second plate can also include a polymer material around the holes, and threads on an orthopedic screw can engage (e.g., cut into) the polymer materials to fix the orientation of the plates 200.

The body section 204 can also include one or more raised features 212 (one of which is labeled for clarity) that extend from the body portion 204. In some cases, each raised feature 212 can extend a same distance from the body portion 204. The raised features can each have a height (e.g., distance from the body portion) that is equal to a height of a corresponding arm 206. Accordingly, when the plate 200 is placed against a bone, the plate 200 will sit flush against due to the equal height of the raised features 112 and the clamp 208 with respect to the body portion 204. In these cases both the clamps 202 and the raised features 212 may contact the bone when the plate 200 is placed against a bone. In other cases, different raised features 212 can extend different distances from the body portion 204. The raised features 212 can be positioned at various locations along the body portions. In some examples, the raised features 212 can be positioned between holes 210 on the body portion, which may constrain movement of a second plate with respect to the plate 200.

In some cases, the raises features 212 constrain movement of a first plate 200 relative to a second plate. For example, the raised features 212 can substantially limit rotation of a first plate 200 with respect to a second plate, which may aid fixing multiple plates together to create a rigid assembly and also aid fixing multiple bone fragments to aid healing in a desired orientation.

The plate 200 can include one or more relief features 214 (one of which is labeled for clarity), which can be located along the body portion 204 and/or the clamp 202. The relief features 214 can be configured to facilitate bending of the plate 200. For example, the relief features 214 can more easily bend under stress (e.g., from a user) than other segments of the plate, which may allow a surgeon to bend the plate 200 to a desired configuration.

In some cases, one or more of the holes 208 and/or 210 may be configured as compression holes, which can cause two bone segments to be compressed or brought together using an orthopedic fastener. For example, one or more of the holes 208 and/or the holes 210 may have a non-circular shape (e.g., elliptical, tear-drop, and/or the like), and when an orthopedic fastener is engaged with the hole 208, 210 it can cause the screw to compress and/or shorten a distance between two bone segments.

Figure 3:
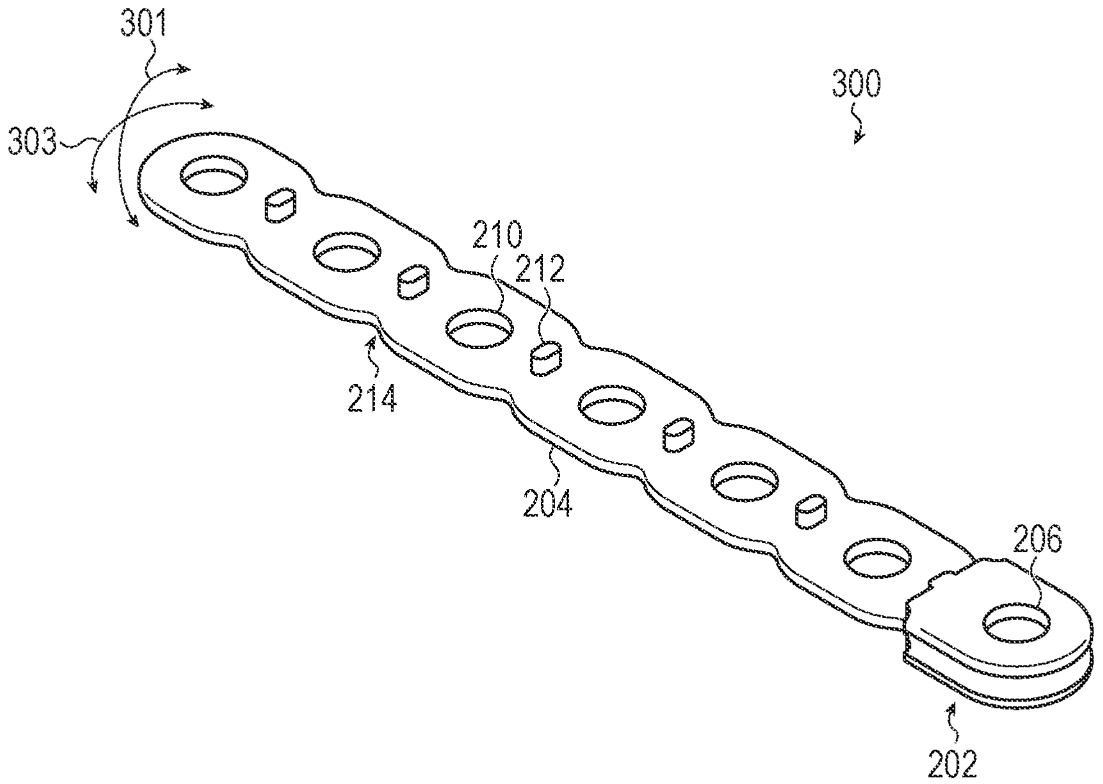
FIG. 3 shows an example of an orthopedic plate.

FIG. 3 shows an example of an orthopedic plate 300 that can be used to create an assembled plate system such as the orthopedic plate assembly 100. The orthopedic plate 300 can be an example of the plates described herein, for example plate 200. The plate 300 can include a single clamp 202 and a body portion 204. The clamp 202 may be located on a first end of the plate 300 and the body portion 204 may define a second end of the plate 200. Accordingly, the clamp 202 of the plate 300 may attach to a body portion defining an end of a second plate 300. The clamp 202 can couple the plate 300 to other plates and the plate 300 can couple to other single clamp plates, double clamp plates, or plates with other shapes and/or clamp configurations as described herein. In other cases, the plate 300 may not include a clamp 202 and the plate comprises only a body section 204. In examples where the plate 300 does not have a clamp 202, the plate 202 may take on a variety of configurations, for example, curved, multi-segmented and so on, as described herein.

In some cases, the plate 300 can include different lengths, different numbers, and/or configurations of holes 210, different numbers and/or configurations of raised features, and/or different shapes. For example, the body portion 204 can include a series of holes 210 (one of which is labeled for clarity) that are each separated by a raised feature 212. In some cases, the holes 210 can be positioned in other configurations, such as closer together, offset from each other (e.g., towards a side or different sides of the body portion 204), and/or the like. Additionally or alternatively, the raised features 212 can have different configurations. For example, the raised features can be placed at different positions, on one side of the plate, spaced further apart, have differing heights, and/or the like.

The plate 300 can also be configured to be bent by a user. For example, the plate 300 can be bent along a first direction 301, bent along a second direction 303, and/or otherwise twisted or manipulated to a desirable shape by a user. In some cases, the size (e.g., thickness, width, etc.), shape, and/or material can be configured to facilitate bending of the plate 300. For example, the relief features 214 may reduce an amount of force required to bend the plate, for example, along the first direction 301 and/or the second direction 303. Additionally or alternatively, the relief features 214 can cause the plate 300 (or plate 200) to bend in specific locations, for example the plate 300 may experience more deformation in the region of the relief features 214.

Figure 4:
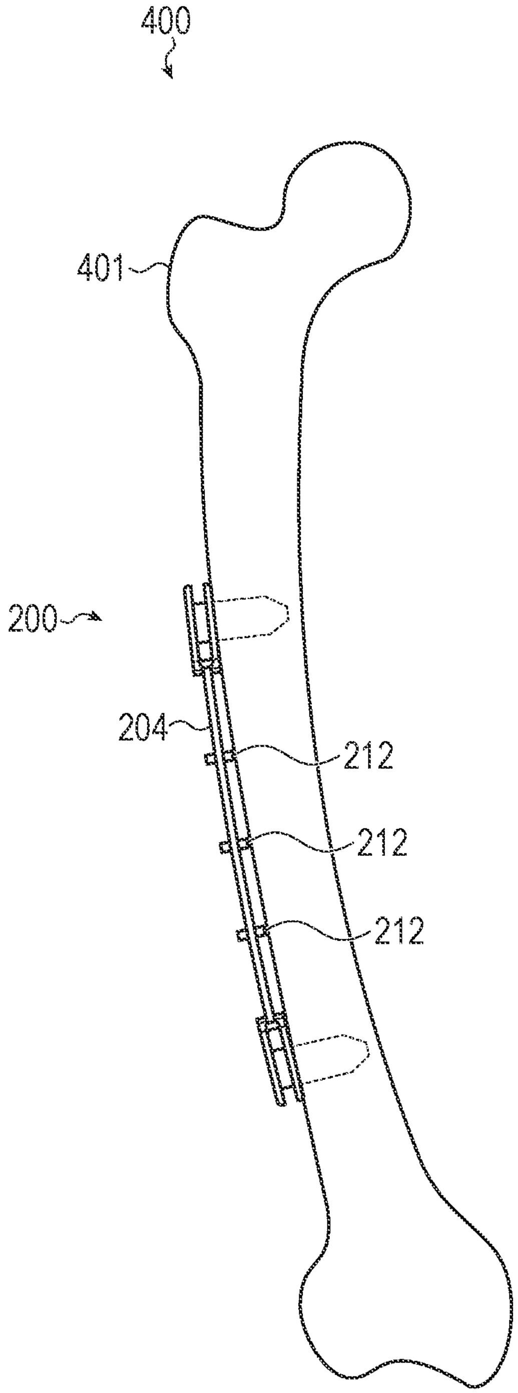
FIG. 4 shows an example of an orthopedic plate anchored to a bone.

FIG. 4 shows an example of the plate 200 anchored to a bone 401. In some cases, the raised features 212 may contact the bone 401 to support the plate 200 and offset the body portion 204 from the bone 401. These raised features 212 may allow other plates to be attached to the plate 200, without causing a high spot, for example caused by a clamp of another plate. Additionally or alternatively, the raised features 212 may provide additional contact points with the bone, which can help stabilize the plate 200 and/or the assembly. In some cases, the raised features 212 can include structures that help couple the plate 200 to the bone. For example, the raised features 212 can include sharp edges, coregulations, knurling, or other suitable features that help prevent the plate 200 and/or assembly from moving once positioned on the bone 401.

In some cases, the plate 200 can have a preconfigured curvature or other shape as described herein. Additionally or alternatively, the plate 200 can be bent or otherwise deformed, which may be used to match the shape of the plate 200 to the shape of a particular bone segment and/or desired shape for a fractured bone.

Figure 5:
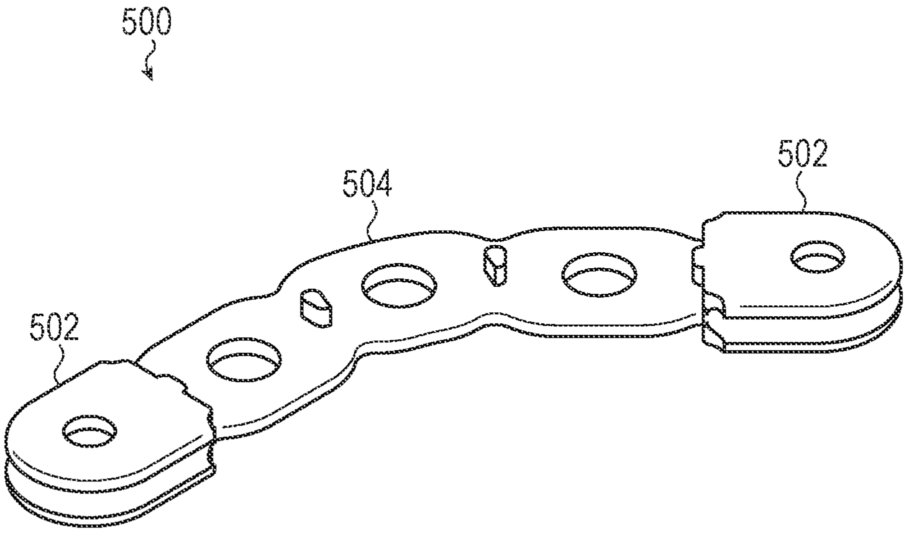
FIG. 5 shows an example of an orthopedic plate.

FIG. 5 shows an example of an orthopedic plate 500 that has a curved shape. The orthopedic plate 500 can be an example of the orthopedic plates described herein, such as plate 200 and 300. The plate 500 can include one or more clamps 502 and a body section 504, which can be examples of the clamps and body sections described herein. The orthopedic plate 500 shows an example of a curved plate, and other configurations and shapes are possible, such as differently shaped curves, multiple curved sections, combinations of different types of shapes, such as curved and straight sections, or any other suitable variations.

Figure 6:
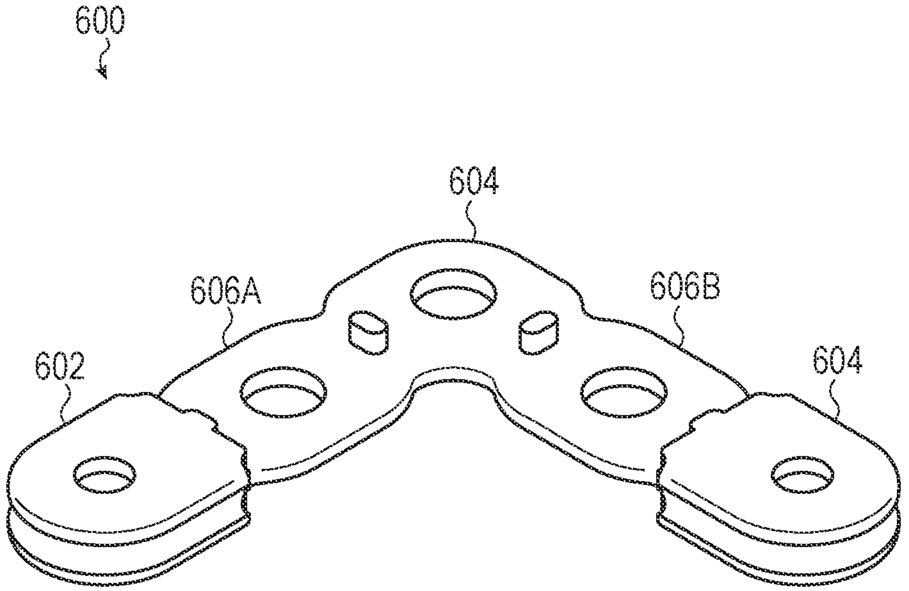
FIG. 6 shows an example of an orthopedic plate.

FIG. 6 shows an example of an orthopedic plate 600 that has an angled shape. The orthopedic plate 600 can be an example of the orthopedic plates described herein, such as plates 200 and 300. The plate 600 can include one or more clamps 602 and a body section 604, which can be examples of the clamps and body sections described herein. The plate 600 shows an example of a body section that includes a first segment 606*a* that is positioned at an angle with respect to a second segment 606*b*. The first and second segments 606*a*, 606*b* can be positioned at various angles with respect to each other.

Figure 7:
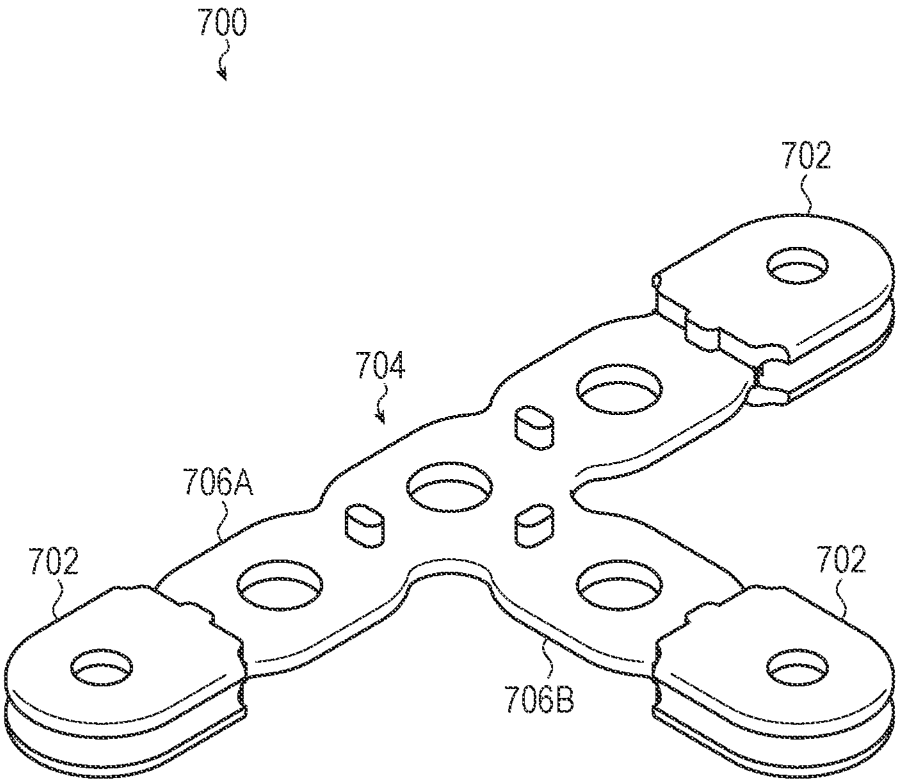
FIG. 7 shows an example of an orthopedic plate.

FIG. 7 shows an example of an orthopedic plate 700 that has more than two end segments. The orthopedic plate 700 can be an example of the orthopedic plates described herein, such as plates 200 and 300. The plate 700 can include one or more clamps 702 and a body section 704, which can be examples of the clamps and body sections described herein. The body section 704 can include multiple sections 706, which can each have a coupling feature. In some cases, the coupling feature at the end of each section can be a clamp 702 and in other cases the coupling feature can be a portion of the body section 704 such as described herein (e.g., plate 300 shown in FIG. 3). The example plate 700 has a first body section 706*a* and a second body section 706*b* oriented at a normal angle. In other examples the plate 700 can include additional body sections, which can be orientated at a variety of different angles with respect to each other.

Figure 8A:
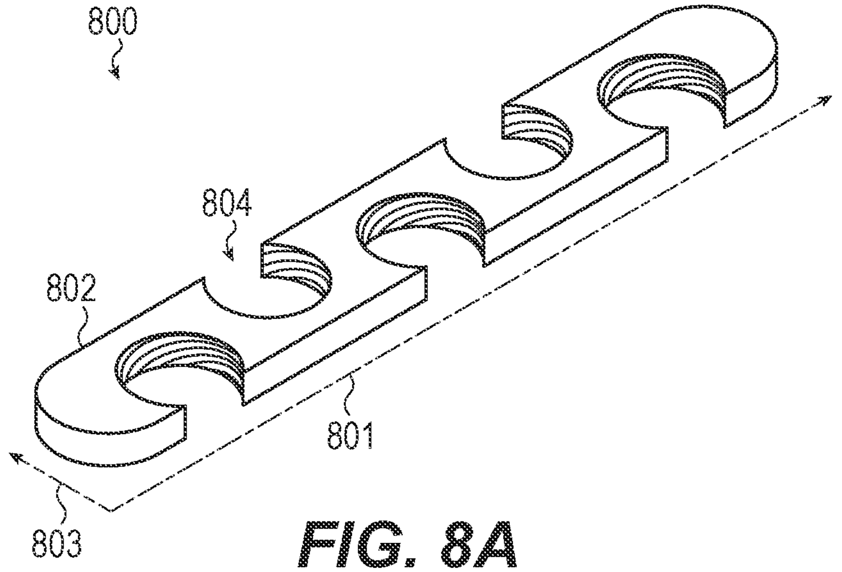
FIGS. 8A and 8B show perspective and top views of an example orthopedic plate.
Figure 8B:
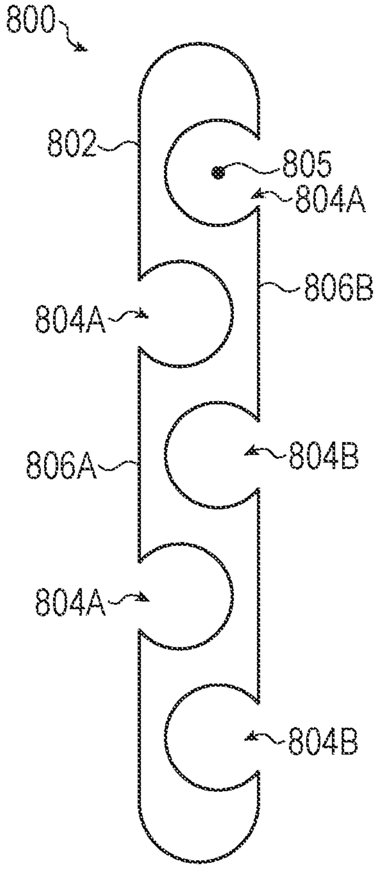

FIGS. 8A and 8B show perspective and top views of an example orthopedic plate 800. The plate 800 can have a body section 802 that defines a set of locking features 804 (one of which is labeled for clarity). The locking features 804 can be positioned along the sides 806 of the body section and include semi-circular holes extending through a thickness of the body section 802. In some cases, a length dimension 801 of the body section 802 can be greater than a width dimension 803 of the body section 802.

As shown in FIG. 8B, a first set of locking features 804*a* can be positioned along a first side 806*a* of the body section 802 and a second set of locking features 804*b* can be positioned along a second side 806*b* of the body section 802. In some cases, holes of the first set of locking features 804*a* can alternate with holes of the second set of locking features 804*b*. This may allow the locking features 804 to be placed closer together, which can help increase the amount of fastening locations in a given area.

The locking features 804 can be semicircular holes, where a portion of the hole does not have a sidewall. In some cases, a center point 805 of each of the locking features 804 can be positioned within a side 806 of the body section 802. Accordingly, the sidewall of each semicircular hole may extend greater than 180 degrees around the perimeter of each hole, to retain an orthopedic anchor, such as an orthopedic screw within the locking feature 804 without completely surrounding the anchor.

In some cases, the locking features 804 may extend greater than halfway across the width 803 dimension of the body section 802, which may help to reduce the width of the body section 802 compared to a diameter of an orthopedic anchor. In some cases, the plate 800 can include different shapes, and/or configurations such as described herein. For example, the plate 800 can be curved along its length dimension 801, have multiple connected segments, or have different segments that are angled with respect to each other. Additionally or alternatively, the plate 800 can include one or more coupling mechanisms, such as the clamps described herein, which may allow multiple plates 800 to be coupled together to create an assembled plate structure.

In some cases, the locking features 804 can be threaded semi-circular holes that are configured to engage with threads on the head of an orthopedic anchor, such as a locking orthoepic screw. In other cases, the locking features can include a second material such as an over molded polymer, and threads on a locking orthopedic screw can cut into the polymer material to lock the plate 800 with respect to the screw.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An orthopedic fixation system, comprising:
first and second plates each defining:
a clamp positioned at an end of a respective plate and defining a first hole;
a body portion extending from the clamp and comprising one or more holes; and
one or more raised features positioned along the body portion; wherein:
the clamp of the first plate is configured to be positioned between adjacent raised features of the one or more raised features of the second plate and couple with the body portion of the second plate; wherein:
the first hole is configured to align with a second hole of the one or more holes; and
the first and second plates are rigidly coupled by an orthopedic screw engaging the first and second holes when the orthopedic fixation system is coupled to a user.

2. The orthopedic fixation system of claim 1, wherein:
the clamp comprises a first arm separated from a second arm by a gap;
the first arm comprises the first hole;
the second arm comprises a second hole that aligns with the first hole; and
the first and second arms are positioned on opposite sides of the body portion when the first plate is coupled to the second plate.

3. The orthopedic fixation system of claim 1, wherein:
the first hole is a threaded hole; and
the second hole is an unthreaded hole.

4. The orthopedic fixation system of claim 1, wherein the orthopedic screw is a locking orthopedic screw.

5. The orthopedic fixation system of claim 1, wherein the one or more raised features each extend a same distance from the body portion.

6. The orthopedic fixation system of claim 5, wherein each of the one or more raised features is positioned between adjacent holes of the one or more holes.

7. The orthopedic fixation system of claim 1, wherein the first plate can be rotated with respect to the second plate when the first hole is aligned with the second hole.

8. The orthopedic fixation system of claim 1, wherein at least one of the first plate or the second plate is curved along its length.

9. An orthopedic plate system, comprising:
a first plate defining:
a first body portion;
a set of first holes positioned along the first body portion; and
a set of first raised features, each of the first raised features positioned between adjacent holes of the set of second holes; and
a second plate defining:
a second body portion;
a set of second holes positioned along the second body portion; and
a set of second raised features, each of the second raised features positioned between adjacent holes of the set of second holes; and
one or more raised features positioned along the second body portion; and
a clamp positioned at an end of the second body portion and defining a first hole of the set of first holes, the clamp configured to couple to the first body portion of the first plate; wherein:

when the clamp is coupled to the first body portion of the first plate, the first hole aligns with a second hole of the set of second holes; and the first hole and the second hole are configured to engage with an orthopedic screw.

10. The orthopedic plate system of claim 9, wherein inserting the orthopedic screw into the first and second holes rigidly fixes the first plate with respect to the second plate.

11. The orthopedic plate system of claim 9, wherein the clamp is positioned between adjacent raised features of the one or more raised features when the first hole is aligned with the second hole.

12. The orthopedic plate system of claim 9, wherein the second plate is configured to be rotated with respect to the first plate when the first hole is aligned with the second hole.

13. The orthopedic plate system of claim 9, wherein a length of the first plate is different from a length of the second plate.

14. The orthopedic plate system of claim 9, wherein a shape of the first plate is different from a shape of the second plate.

15. The orthopedic plate system of claim 9, wherein:

the first plate comprises one or more relief features positioned along the first body portion; and the first plate is configured to bend at the one or more relief features.

* * * * *